(12) United States Patent
Abernathie et al.

(10) Patent No.: US 8,057,548 B2
(45) Date of Patent: Nov. 15, 2011

(54) SPINAL FUSION CAGE, METHOD OF DESIGN, AND METHOD OF USE

(76) Inventors: Dennis Lee Abernathie, Columbia, MO (US); Ferris Michael Pfeiffer, Boonville, MO (US)

( * ) Notice: Subject to any disclaimer, the term of this patent is extended or adjusted under 35 U.S.C. 154(b) by 1426 days.

(21) Appl. No.: 11/551,597

(22) Filed: Oct. 20, 2006

(65) Prior Publication Data

US 2007/0043442 A1 Feb. 22, 2007

Related U.S. Application Data

(63) Continuation-in-part of application No. 11/081,162, filed on Mar. 16, 2005, now Pat. No. 7,780,732.

(51) Int. Cl.
*A61F 2/44* (2006.01)

(52) U.S. Cl. .................................. 623/17.16; 606/246

(58) Field of Classification Search ..... 623/17.11–17.16
See application file for complete search history.

(56) References Cited

U.S. PATENT DOCUMENTS

| | | | |
|---|---|---|---|
| 6,217,579 B1 * | 4/2001 | Koros | 623/17.11 |
| 6,641,614 B1 * | 11/2003 | Wagner et al. | 623/17.15 |
| 7,780,732 B2 * | 8/2010 | Abernathie | 623/17.11 |
| 2003/0074063 A1 * | 4/2003 | Gerbec et al. | 623/16.11 |
| 2003/0074064 A1 * | 4/2003 | Gerbec et al. | 623/16.11 |
| 2006/0122701 A1 * | 6/2006 | Kiester | 623/17.11 |

* cited by examiner

*Primary Examiner* — Nicholas Woodall (57) ABSTRACT

A fusion cage of the present invention includes a first housing portion, a second housing portion, and an insert portion adapted to be received therebetween, wherein the geometry of the fusion cage corresponds substantially to the geometry of a void into which the fusion cage is to be inserted. Also described is a novel tool for insertion of a fusion cage and a novel method for designing a fusion cage or other surgical implant for filling a void identified within a patient.

10 Claims, 11 Drawing Sheets

SPINAL FUSION CAGE, METHOD OF DESIGN, AND METHOD OF USE

CROSS-REFERENCE TO RELATED APPLICATIONS

This application is a continuation-in-part of U.S. patent application Ser. No. 11/081,162, filed on Mar. 16, 2005 now U.S. Pat. No. 7,780,732. U.S. patent application Ser. No. 11/081,162 is hereby incorporated herein by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

The present invention relates generally to an implantable device for promoting the fusion of adjacent bony structures, and a method of using the same. More specifically, the present invention relates to an expandable fusion cage that may be inserted into an intervertebral space, and a method of using the same.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

The majority of spinal fusion cages are placed in front of the spine, a procedure known as anterior lumbar interbody fusion, or ALIF. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back.

Regardless of the approach, the typical procedure for inserting a common threaded and impacted fusion cage is the same. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space.

Although ALIF is common, the procedure suffers from disadvantages. In cases where patients have a "tall" disc, or where there is instability (such as with isthmic spondylolistheses), an anterior approach to the spinal fusion may not provide adequate stability. Further, the procedure is performed in close proximity to the large blood vessels that go to the legs, thereby risking damage to these blood vessels, which can result in excessive blood loss. In dealing with male patients, another unique risk arises. Approaching the L5-S1 disc space from the front risks a condition known as retrograde ejaculation. This is due to the position of small nerves directly over the disc interspace that control a valve causing the ejaculate to be expelled during intercourse. Dissecting over the disk space can cause the nerves to stop working and, absent innervation to the valve, the ejaculate may move into the bladder.

A problem common to many fusion cages, regardless of method of insertion, concerns maintaining or restoring the normal anatomy of the fused spinal segment. Once a disc or a portion thereof is removed, the normal lordotic or kyphotic curvature of the spine is eliminated. Traditional fusion cages neglect the need to correct this curvature. Such cages may lead to a kyphotic deformity as the vertebrae settles around the implant. Often, revision surgeries are necessary to correct spinal imbalances. Fusion cages have been designed having a wedge-like shape in order to address these issues, but because of the shape of the cage, such devices must heretofore have been implanted using an ALIF procedure, thereby suffering from all of the disadvantages of using that procedure.

A problem with existing titanium cages is that it is difficult to assess spinal fusions postoperatively because the metal of the cage interferes with attempts to evaluate the fusion by x-ray. Radiolucent cages, such as those made from either carbon fiber or polyetheretherketone (PEEK), have been used to provide better postoperative visualization of spinal fusions. A problem with such cages, however, is that they do not adhere well to the bony endplates and thus often must be supplemented with pedicle screws.

What is needed, therefore, is a spinal fusion cage suitable for a PLIF procedure that allows for preservation or restoration of the proper lordotic or kyphotic curvature of the spine, provides adequate strength and stability to be used with or without supplements such as pedicle screws, and that can be visualized postoperatively via radiologic procedures such as x-rays and the like. What is further needed is a fusion cage adapted to remain within an intervertebral space, designed to match the natural curvature of the adjacent vertebrae, and an insertion tool adapted to easily insert such a fusion cage into an intervertebral space. Furthermore, a method is needed for producing a fusion cage having the above characteristics, as well as for producing other implantable devices conforming to the shape of the space to be occupied by the device.

BRIEF SUMMARY OF THE INVENTION

The present invention provides, in one aspect, a fusion cage including a first housing, a second housing, and an insert portion adapted to be received therebetween, wherein the fusion cage has a geometry that corresponds substantially to a geometry of a void into which the fusion cage is to be inserted.

In another aspect of the present invention, each of the housing portions of the fusion cage includes at least one aperture for allowing bone growth therethrough.

In another aspect of the present invention, at least one of the housing portions includes a stop to prevent insertion of an insert portion beyond an edge of the housing portions.

In another aspect of the present invention, the housing portions of the fusion cage include at least one ridge extending across at least a portion of the exterior surface thereof to prevent backwards motion of the fusion cage when inserted into a space between adjacent vertebrae.

In another aspect of the present invention, the housing portions and insert portions include engaging lock portions that lock the insert portion in place once properly positioned between the two housing portions.

In another aspect, the present invention provides a tool for insertion of a fusion cage, the tool including a shaft portion, a plunger portion located within the shaft portion and slidingly maneuverable therein, and tab portions having posts that are adapted to engage the apertures in the housing portions of a fusion cage. The plunger portion is adapted to releasably engage an insert portion of a fusion cage.

In another aspect of the present invention, a method of designing a fusion cage or other surgical implant is provided, the method including identifying a void into which an implant is to be inserted, creating a model of the void, extracting the geometry of the void from the model, obtaining a plurality of geometries from a predetermined number of patients, using the geometries extracted to create an averaged surface, and designing a geometry of a surgical implant to correspond substantially to the geometry of the void based on the averaged surface.

DETAILED DESCRIPTION OF THE INVENTION

Before turning to a detailed description of the present invention, it should be noted that the terms "upper" and "lower" are used herein to distinguish various features or parts of the present invention. As these words are used herein, they refer to the relative position of the described part when implanted into a human body, and when that human body is erect. The terms are used for clarity of understanding only, and are not intended to place any specific limitations on the invention described herein. The same holds true for other variations on the words "upper," "lower," "upward," "downward," and the like.

The phrase "interior surface" or some variant thereof is also used herein, and refers generally to a surface of a device that disposed toward an interior of the device when the device is assembled.

The phrase "fixedly attached" is used herein to indicate a fixed attachment of any sort (i.e. one that is not readily releasable with damaging the device). It is contemplated that the phrase fixedly attached, when used in relation to two or more portions of the present invention, includes portions that are formed from a single, contiguous piece of material, such as a synthetic polymer. Such portions are considered fixedly attached to one another even though they represent a single piece of material rather than a physical attachment such as by adhesive or the like.

Figure 1:
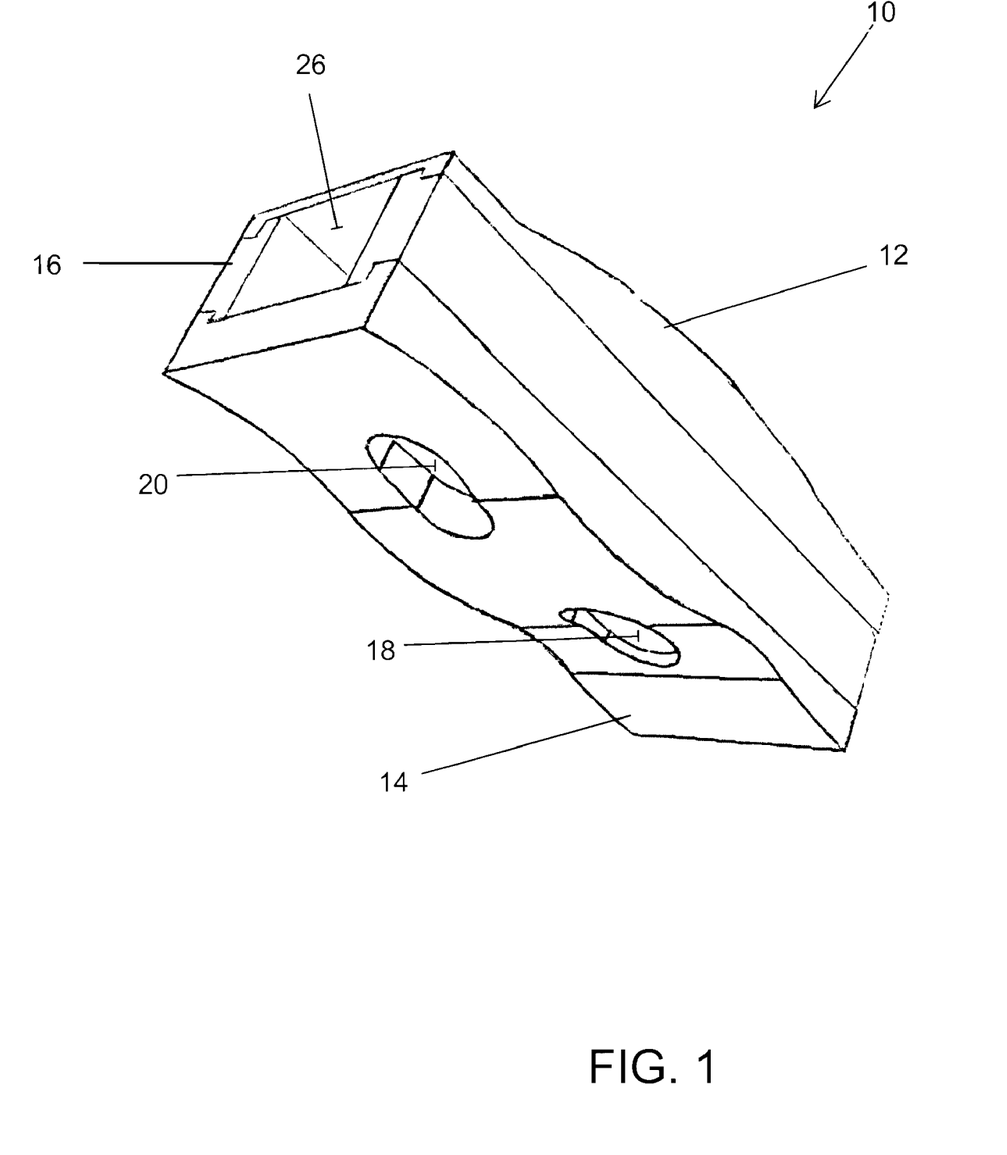
FIG. 1 is a perspective view of one embodiment of a fusion cage constructed in accordance with the teachings of the present invention.

The several embodiments of the fusion cage of the present invention are shown in the figures, wherein like numerals indicate like parts. Turning now to FIG. 1, there is provided one embodiment of a fusion cage constructed in accordance with the teachings of the present invention. Fusion cage 10 includes generally an upper housing portion 12, a lower housing portion 14, an insert portion 16, two apertures 18 and 20 in lower housing portion 14, and two apertures 22 and 24 (not shown in FIG. 1) in upper housing portion 12.

Although device 10 is operable and may be used in accordance with the principles of the present invention, it is shown here primarily to illustrate certain novel features of a fusion cage constructed in accordance with the teachings of the present invention, these novel features being the results of an unexpected finding by the Applicant. Before turning to these novel features, however, a general explanation of the use of the device of FIG. 1 is now provided.

Housing portions 12 and 14 are preferably inserted into the space between two adjacent vertebrae (a space created by the removal of an intervertebral disc from the spine) absent insert portion 16, by use of distracting forceps, a specialized insertion tool, or any other suitable method of insertion. Once housing portions 12 and 14 are in place, a tool is used to push insert portion 16 into place between the two housing portions, thereby displacing the housing portions and causing the housing portions to abut the surfaces of the adjacent vertebrae. Apertures 18, 20, 22, and 24 allow the growth of bone through fusion cage 10, thereby allowing the adjacent vertebrae to fuse to one another with fusion cage 10 in place.

The above-described process is provided to establish a general principle of use of a fusion cage constructed in accordance with the teachings of the present invention. Further detail with respect to this use, as well as tools provided herein for use with a fusion cage according to the present invention, is provided below.

One novel aspect of the present fusion cage, in its various embodiments, lies in the curvature of the upper and lower housing portions 12 and 14. It has been discovered by the applicant that the curvature of the upper and lower surfaces of adjacent vertebrae is, unexpectedly, substantially preserved from person to person. Applicant has made this discovery by using a computer and associated software and imaging technology to digitize the bone structure, specifically vertebral structure, of a number of persons. After digitization, the void between the adjacent vertebrae was analyzed for shape, as well as other features, and the results from various persons were compared for similarities. Upon comparison, it was discovered that the shape of the void between adjacent vertebrae, and of the upper and lower surfaces of adjacent vertebrae, is substantially conserved from person to person. With this knowledge, the upper and lower housing portions 12 and 14 were provided having a curvature that is substantially the same as the curvature found in the preceding analysis. Thus, the unique curvature of the housing portions of the present device corresponds substantially to the shape of the void between the vertebrae of a given person, making the present device uniquely suited as a spinal fusion cage that, among other things, allows for proper lordosis of the spine.

The method used to obtain the curvature of upper and lower housing portions 12 and 14, shown in the drawings, is described in further detail below. The present device, as shown in the figures, is adapted primarily for use in the lumbar spine, though the design principles underlying the present invention may be used to produce fusion cages or other devices for use elsewhere in the spine or body.

Figure 2:
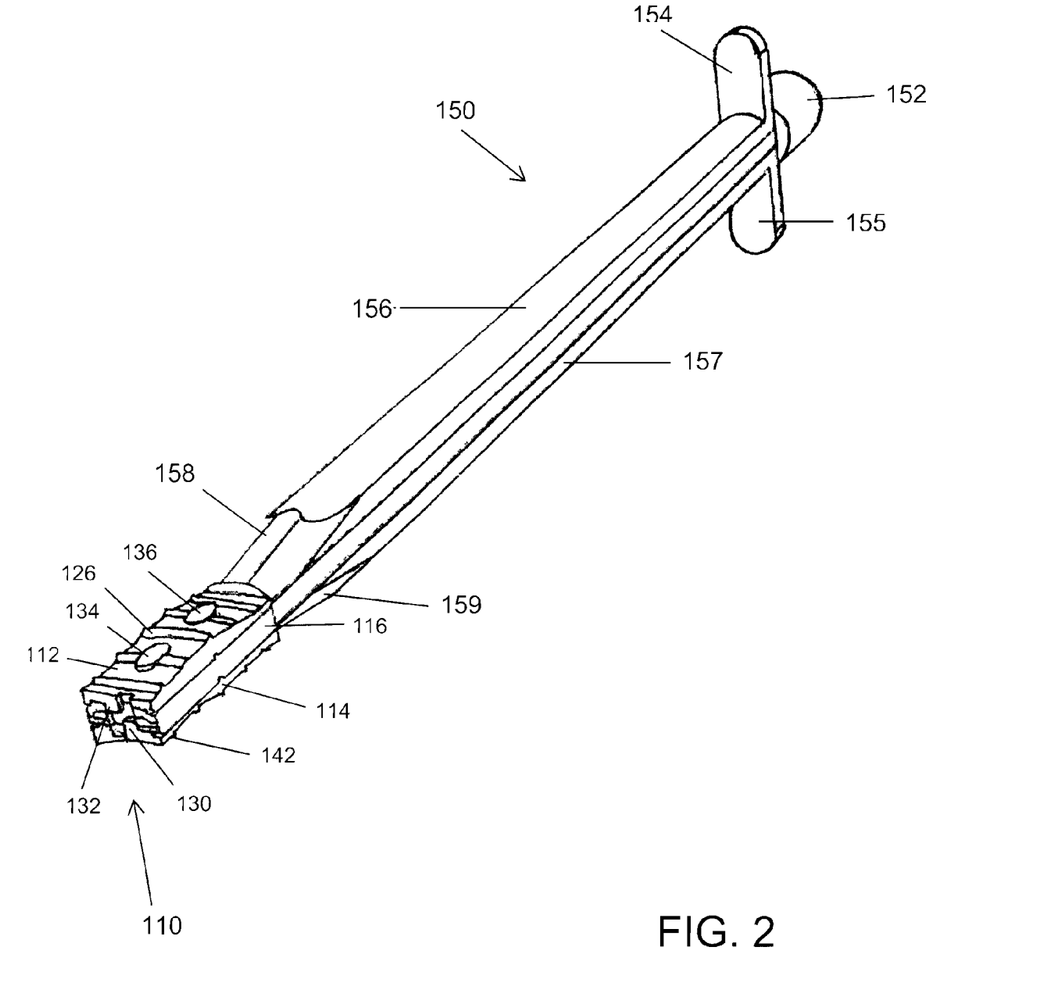
FIG. 2 is a perspective view of another embodiment of a fusion cage constructed in accordance with the teachings of the present invention, the fusion cage being engaged with an insertion tool also constructed as taught herein.

FIG. 2 provides a perspective view of one embodiment of a fusion cage 110 constructed in accordance with the teachings of the present invention, the fusion cage 110 being associated with a novel insertion tool 150. Upper and lower housing portions 112 and 114 of fusion cage 110 preferably retain the same curvature as described with respect to fusion cage 10 for the reasons provided above, though it is contemplated that a fusion cage having a conventional shape known in the art may be adapted for use with the present tool and method. The features of fusion cage 110 will be described in greater detail with respect to FIG. 3, below.

As seen in FIG. 2, a specialized, novel tool 150 is used for the insertion of fusion cage 110 into a space between adjacent vertebrae. Insertion tool 150 includes two semi-cylindrical shaft portions 158 and 159, two fin portions 154 and 155, and a knob portion 152. Shaft portions 158 and 159 preferably include reinforced portions 156 and 157, adapted to withstand pressure placed on device 150 by a user of said device during normal use. Other portions of insertion tool 150 are described with respect to FIG. 4, below.

Insertion tool 150 includes a plurality of protruding posts, such as upwardly protruding posts 134 and 136, by means of which insertion tool 150 engages the housing portions of fusion cage 110. Upwardly protruding posts 134 and 136 engage upper housing portion 112. Downwardly protruding posts 138 and 140 are provided for engagement of lower housing portion 114, but are not visible in FIG. 2. The relationship between these various protruding posts and the remainder of insertion tool 150 is shown more clearly in FIG. 4 and described below. While insertion tool 150 is shown in the figures as having two upwardly protruding posts and two downwardly protruding posts, it is contemplated that only one of each post may be present, or that more than two of each may be present.

Insert portion 116 is shown in final position between upper and lower housing portions 112 and 114. Initially, however, prior to insertion of insert portion 116 between upper and lower housing portions 112 and 114, insert portion 116 is positioned between shaft portions 158 and 159. Upper and lower housing portions 112 and 114 are, thus, initially adjacent one another.

Insertion tool 150 is used to insert upper and lower housing portions 112 and 114 of fusion cage 110 into a space between two adjacent vertebrae while upper and lower housing portions 112 and 114 are adjacent to one another (i.e. insert portion 116 is not present between upper and lower housing portions 112 and 114, leaving fusion cage 110 in a collapsed form). Upper and lower housing portions 112 and 114 may be inserted into an opening between adjacent vertebrae by simply putting pressure on fin portions 154 and 155 of insertion tool 150, by putting pressure on knob 152, by using a small hammer or other instrument to tap fin portions 154 and 155 and/or knob 152, by any combination of these, or by any other suitable method for completing the insertion of upper and lower housing portions 112 and 114 into a space between adjacent vertebrae using insertion tool 150. Once insertion is accomplished, upper and lower housing portions 112 and 114 may be further aligned by placing pressure on, or tapping, either upper fin portion 154 or lower fin portion 155, or both, depending on the alignment desired or required. In this way, precise placement of upper and lower housing portions, and therefore of fusion cage 110, may be achieved.

Once upper and lower housing portions 112 and 114 are properly positioned, knob 152 may be utilized to force insert portion 116 between the two housing portions, thereby expanding device 110 such that upper housing portion 112 is in contact with a lower surface of a vertebra immediately above the device and lower housing portion 114 is in contact with an upper surface of a vertebra immediately below the device. The novel curvature of the two housing portions will correspond substantially to the curvature of the surfaces of the vertebrae being contacted.

Figure 3:
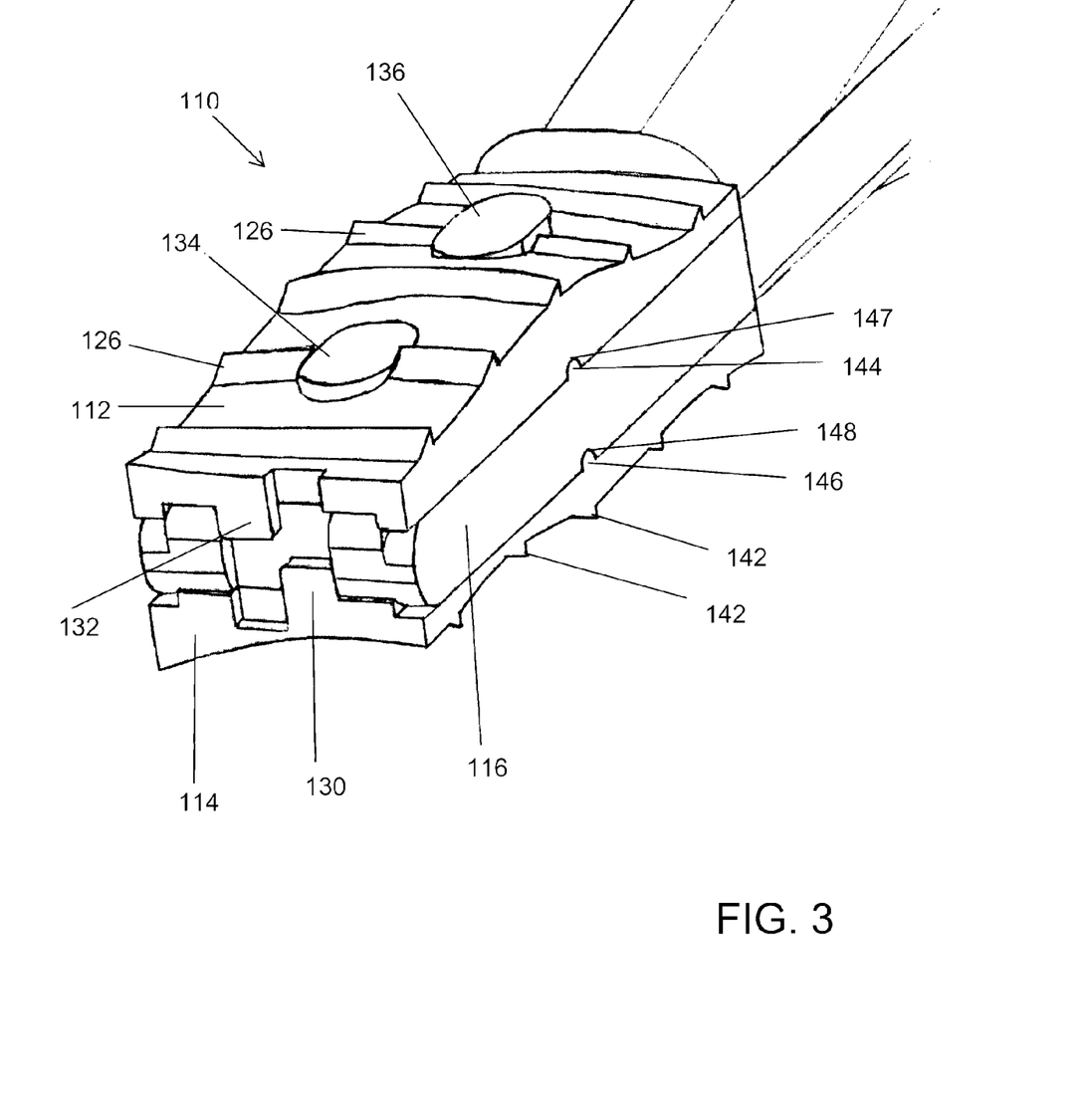
FIG. 3 is a magnified perspective view of the fusion cage of FIG. 2 shown engaged with an insertion tool.

FIG. 3 provides a perspective view of a fusion cage 110 constructed in accordance with the teachings of the present invention. Fusion cage 110 is shown in greater detail so that certain features of the device may be more clearly shown and commented upon. Upper housing portion 112, for example, preferably includes a plurality of ridges 126 disposed along an outer surface thereof and in such a manner as to prevent backward motion of upper housing portion 112 when upper housing portion 112 is in contact with a vertebral surface. Likewise, lower housing portion 114 preferably includes a plurality of ridges 142 disposed along an outer surface thereof an in such a manner as to prevent backward motion of lower housing portion 114 when lower housing portion 114 is in contact with a vertebral surface. Although multiple ridges 126 and 142 are shown in the drawings, it is contemplated that a single ridge may be utilized on each housing portion, or that the ridges may be lacking entirely. In embodiments wherein ridges are present, it is contemplated that the ridges may extend across the width of the housing portions, as shown, or across any fraction of the width of the housing portion. Although ridges are described here and shown in the figures, any suitable method of preventing or hindering backwards motion of the fusion cage may be employed.

Also shown in FIG. 3 are lower stop 130 and upper stop 132. These stops are preferably protrusions formed as part of the shape of upper and lower housing portions 112 and 114. In the case of upper housing portion 112, upper stop 132 extends in a downward direction, whereas in the case of lower housing portion 114, lower stop 130 extends in an upward direction. These stops serve to contain insert portion 116 within device 110 and insure that insert portion 116 does not extend beyond the boundaries of upper and lower housing portions 112 and 114 when force is applied to insert portion 116 in order to expand device 110 and move insert portion 116 into place. In furtherance of this same goal, insert portion 116 is preferably provided with a raised portion 144 and a groove or notch 148. Lower housing portion 114 is preferably provided with a raised portion 146 that is adapted to be received by groove 148 of insert portion 116. Upper housing portion is preferably provided with a groove 147 adapted to receive raised portion 144 of insert portion 116. As insert portion 116 is being positioned between upper and lower housing portions 112 and 114, being preferably slid into place, raised portion 144 of insert portion 116 engages groove 147 of upper housing portion 112, and raised portion 146 of lower housing portion 114 engages with groove 148 of insert portion 116, locking insert portion 116 into place. It is contemplated that only a single raised portion/groove combination may be utilized (either groove 147 and raised portion 144 or groove 148 and raised portion 146). Alternatively, the raised portion/groove locking mechanism may be eliminated entirely, relying on the aforementioned stops to prevent too much forward movement of insert portion 116. An advantage of the raised portion/groove combination, however, is that unwanted forward and backward motions of insert portion 116 are both prevented. While the stops and raised portion/groove combinations are described herein and shown in the drawings, it is contemplated that any suitable mechanism of locking insert portion into place or preventing unwanted movement may be utilized. In some embodiments, locking mechanisms or mechanisms for hindering unwanted movement of insert portion 116 may be eliminated entirely. Once insert 116 is correctly positioned, knob 152 is retracted, allowing insertion tool 150 to be removed entirely (as described more fully below).

Figure 4:
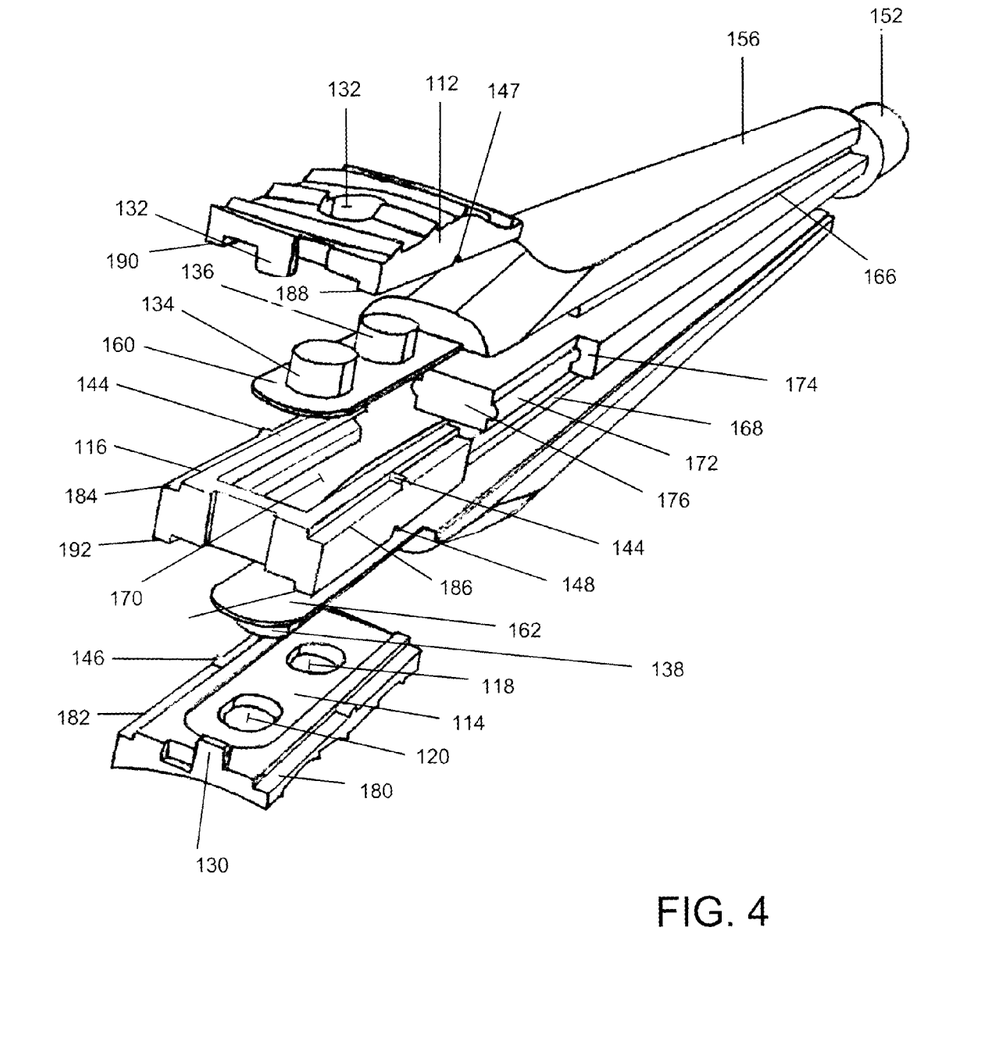
FIG. 4 is an exploded view of a fusion cage and insertion tool constructed in accordance with the teachings of the present invention.

FIG. 4 provides an exploded view of fusion cage 110 and insertion tool 150 in order to clarify the structure of the two and functional relationship therebetween. As can be seen, for example, protruding posts 134 and 136 are preferably located on a tab 160 extending from upper shaft portion 158, and downwardly protruding post 162 is preferably located on a tab 162 extending from lower shaft portion 159. Although not shown, a second downwardly protruding post is also provided in the embodiment of the present invention shown in the drawings.

FIG. 4 also shows features of insert portion 116 not shown in the preceding figures. As shown in the figure, insert portion 116 preferably includes a raised portion 144 upon each of the upper surfaces of the long edges of the insert portion. That is, on either side of insert portion 116 at a point wherein insert portion 116 contacts upper housing portion 112. A groove 148 is likewise preferably present on each of the sides of insert portion 116, except along a lower surface of the long edges of insert portion 116 at points where insert portion 116 contacts lower housing portion 114. Also shown as a feature of insert portion 116 is interior channel 172, which runs along an interior surface of insert portion 116 and along at least a portion of the longitudinal axis thereof. It is preferred that a second interior channel is present along an opposite interior surface of insert portion 116, although this second channel is not shown in the drawing. These interior channels are adapted to receive flanges 172 of plunger 164, allowing insert portion 116 to be mounted thereon. Sidewall 176 of insert portion 116 preferably abuts stop 174 of plunger portion 164 when insert portion 116 is fully mounted thereon. As can be seen, knob 152 is attached to plunger portion 164, and when insert portion 116 is mounted on plunger portion 164, knob 152 can be used to manipulate insert portion 116 and slide it into place between upper and lower housings 112 and 114. After insert portion 116 is correctly positioned, knob 152 may be used to retract plunger 164. This opens an interior space 170 of insert portion 116. Pressure may be applied to reinforced portions 156 and 157 of shaft portions 158 and 159, thereby causing tabs 160 and 162 to move into interior space 170 of insert portion 116 and disengaging protruding posts 134, 136, 162, and, preferably, the second lower protruding post, from the upper and lower housings respectively. Once this is accomplished, insertion tool 150 may be removed from fusion cage 110, leaving fusion cage 110 properly positioned between two vertebrae.

Also shown in FIG. 4 are an upper rail 166 and lower rail 168. Upper and lower rails 166 and 168 are preferably adapted to engage plunger 164, allowing plunger 164 to move along a length thereof by slidingly engaging grooves in the upper and lower surfaces of plunger 164 (not shown). It is preferred that upper and lower rails 166 and 168 are of different radii such that plunger 164, and therefore insert portion 116, can be easily oriented in the proper up-down direction by matching the larger radius rail with the larger groove in the surface of plunger 164 and vice versa. Rails 166 and 168 are preferably constructed as part of the interior surfaces of shaft portions 158 and 159, although they may be provided as separate components or eliminated entirely.

FIG. 4 also illustrates the way in which insert portion 116 aligns properly with upper housing 112 and lower housing 114. This is accomplished by flat surfaces running along each of the long edges of the two housing portions, and these flat surfaces are referred to herein as "channels" even though they are not necessarily enclosed on three sides (although it is contemplated that such U-shaped channels may be used as an alternative to those shown in the figures). Lower housing portion 114, for example, preferably includes two channels 180 and 182 running along opposing long edges of the housing portion. These channels are adapted to receive raised edges 192 and 194 of insert portion 116, raised edges 192 and 194 running along at least a portion of the length of insert portion 116 and along opposing lower edges thereof. Housing portion 112 preferably includes raised edges 188 and 190 running along at least a portion of the length of housing portion 112 and along opposing lower edges thereof. Insert portion 116 preferably includes flat surfaces running along each of the long upper edges of housing portion 116 (said channels also referred to herein as channels), the channels 184 and 186 being adapted to receive raised edges 188 and 190 of upper housing portion 112. The various channels and raised edges may be referred to collectively as aligning portions.

In each of the various embodiments of a fusion cage constructed in accordance with the teachings of the present invention, it is desirable to strike a balance between the strength of the cage and the area available for bone growth. To that end, the apertures in the upper and lower housings are relatively large with respect to the overall surface area of the housings. Likewise, the interior space of the insert portion is relatively large as compared to the size of the insert portion as a whole. This allows a great deal of area for bone growth. It is contemplated that any suitable size or shape of apertures and/or interior space may be utilized, so long as the device has sufficient strength to be useful for its intended purpose. To that end, the materials used to construct the present device may also vary. The housing portions may, for example, be constructed from any polymer, metal, or other material approved for implantation into the human body. A preferred material for the housings is titanium. The insert portion may likewise be constructed from any suitable material approved for implantation into the human body, though it is preferably constructed from polyetheretherketone (PEEK) or other radiolucent material so that a radiologic analysis of the fusion within the cage may be performed. Either of the housing portions or the insert portion may also be constructed from carbon fiber, or may be machined from natural or artificially-produced bone.

Insertion tool 150 is preferably constructed from a synthetic polymer, although any suitable material may be used whether or not approved for implantation into the human body. It is preferred that insertion tool 150 is disposable. The protruding posts of the insertion tool may also be formed from any suitable material, preferably a material that allows the posts to deform enough to fit into the apertures of the housing portions while remaining rigid enough to resist retraction until a user of the tool intends to retract them. It is further preferred that the general shape of insertion tool 150 is cylindrical such that the tool can be inserted through a tube retractor.

Once the present fusion cage device is properly inserted into a space between two adjacent vertebrae, it is preferred that a portion of bone is placed within the device and an end cap is provided to prevent the bone from moving out of the interior of the device. The end cap may be a rigid cap made from polymer or other material, or a gel plug that is positioned such that the bone portion is held within the device. Any other suitable end cap, structure, or other means for partially or completely enclosing an end of the present fusion cage device may also be utilized. Bone morphogenic protein (BMP) may also be provided within the device in order to facilitate bone growth.

Rather than, or in addition to, the ridges present on the housing portions of the present fusion cage device, as described above, other methods of preventing or inhibiting unwanted movement of the device may be utilized. For example, hydroxyapatite may be provided on the surface of the housings or mixed into, for example, a polymer used to create the housings. Alternatively, a smooth cage such as that shown in FIG. 1 may have a screen-like surface to aid in engagement of the vertebral surfaces. As another alternative, the surfaces of the housing portions may be 'bead blasted' with liquid titanium to give a sandpaper-like surface that engages the vertebral surfaces. Any suitable method of inhibiting or preventing unwanted movement of the device may be utilized.

Although the present device is preferably utilized in the lumbar spine, the principles behind the present device are applicable to other areas of the spine as well. That is, in order to match the curvature found in the thoracic or cervical spine, the principles disclosed herein, which include digitizing the bone, analyzing the void between the adjacent vertebrae, and shaping the device to match the void between the adjacent vertebrae, can be utilized to produce devices for use in other areas of the spine. It is contemplated that such a use of the present novel method of designing an implantable device are within the scope of the present invention.

Further, it is contemplated that the principles of the above-described method may be applied to the design of other devices intended to be implanted in spaces between portions of a human or animal body capable of suitable imaging.

The method used to determine the shape of the housing portions of a fusion cage device constructed in accordance with the teachings of the present invention is now described in greater detail. Generally speaking, the method includes surface interpolation in order to generate a surface definition that can be imposed on surgical implants used to fill an anatomic void. The end-result of this process is an implant with optical conformity for a large portion of the population.

The present method begins with the step of identifying the void to be filled by the surgical implant. In the case of a fusion cage device such as described above, the void is created by removing an intervertebral disc from the lumbar spine, thereby creating a void between adjacent vertebrae. It is this void that is filled by the fusion cage. Once the void is identified, a surface curvature representative of a significant portion of the population is determined. In the case of a fusion cage, for example, the surface curvature of interest is that of the superior and inferior surfaces of the intervertebral disc. The curvature of the intervertebral disc matches the curvature of the vertebral endplates. With respect to the fusion cage devices described above, it is preferred that the curvature of the implant (i.e. the surfaces of the upper and lower housing portions) match the curvature of the vertebral endplates.

The surfaces of interest are extracted from 3D geometric models of the void by, for example, CT or MRI scanning, or by any other suitable imaging method. Imaging software is then used to analyze 2D slices of the data and create a 3D solid model of the void. Such imaging software is known in the art, and this general approach to geometry extraction is also known to one of ordinary skill in the art. Once the 3D solid model of the void is created, the 2D slice data is reconstructed to form a 3D surface model of the geometry previously identified. This process is preferably repeated across multiple patient scans to generate a plurality of void geometries that can be combined to form an interpolated surface.

Once the geometry of interest has been extracted using the techniques described above, the desired surfaces are identified and removed from the solid model. This is accomplished using a computer algorithm that performs the following steps: 1) identifies surfaces normal to the patient anatomy; 2) extract normal surfaces from the 3D solid model; 3) applies coordinate transformation to surface data to align surfaces; 4) interpolates and combines surface data from multiple surfaces to create one 'averaged' surface; and 5) outputs surface data for further processing. These steps are preferably applied to a data set that contains multiple void geometries.

Figure 5:
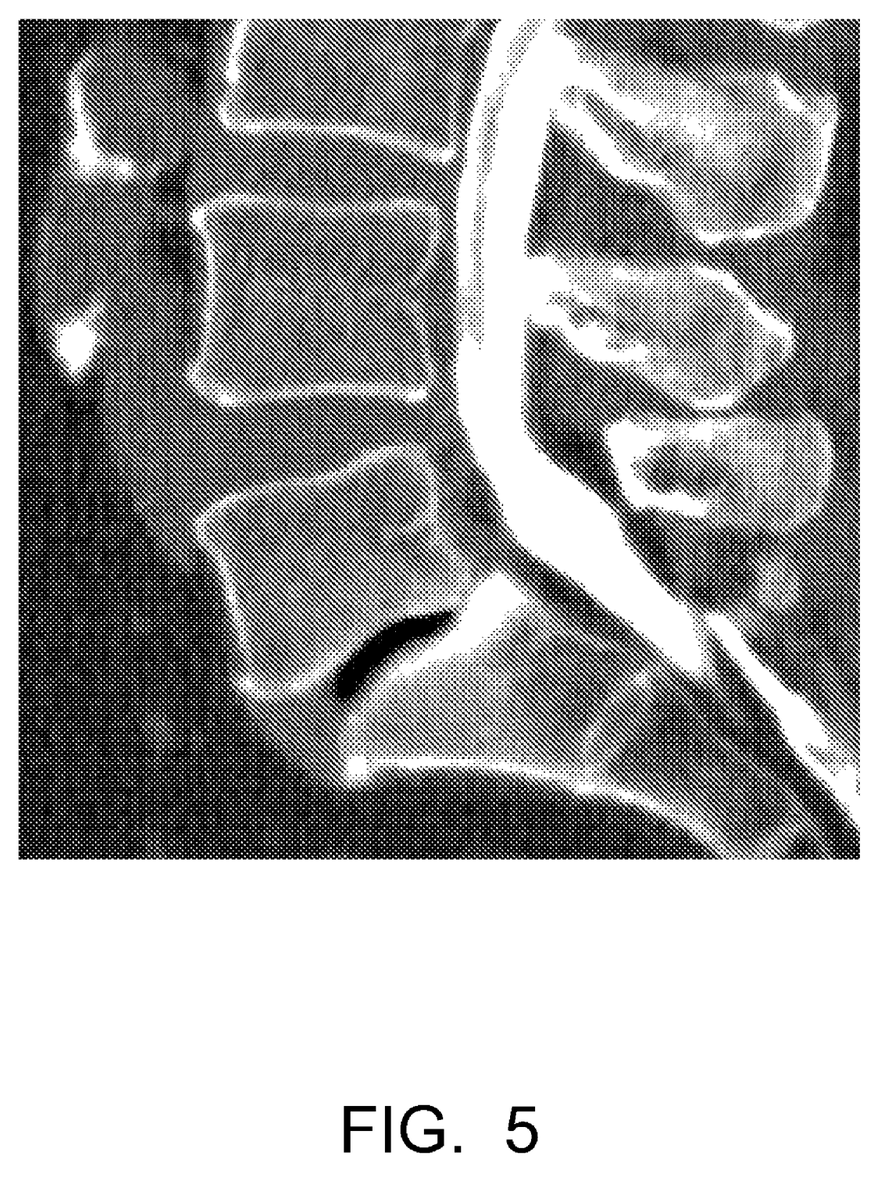
FIG. 5 is a CT scan of a patient anatomy identifying a void between adjacent vertebrae.
Figure 6:
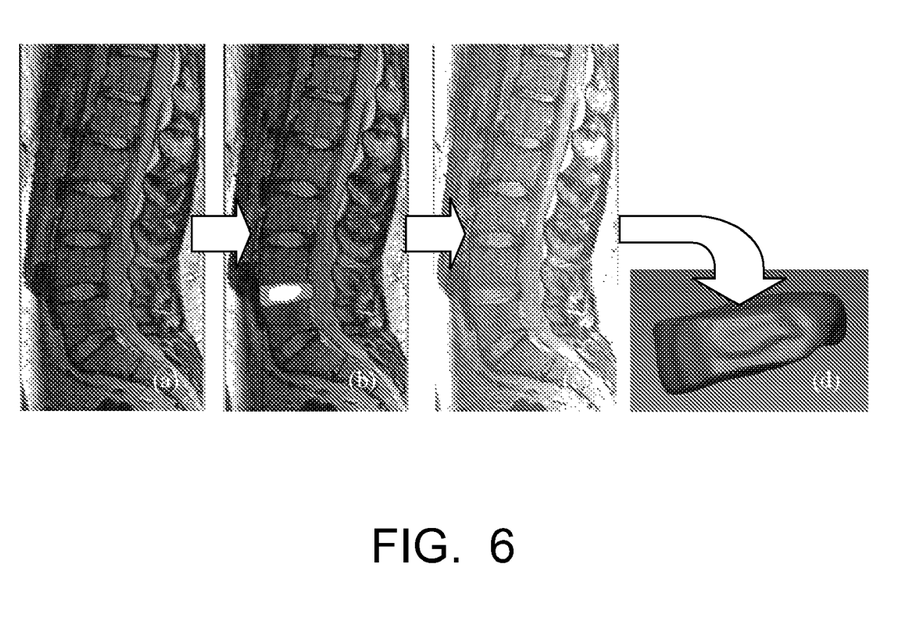
FIG. 6 is an illustration of a void geometry extraction process in accordance with the teachings of the present invention.

FIGS. 5 through 11 are provided in order to supplement the description of the present method provided above with respect to a fusion cage device of the present invention. FIG. 5 is a computer tomography (CT) scan of the lumbar spine with the void area identified therein. FIG. 6 provides an example of the void geometry extraction process. FIG. 6(a) is a patient MRI scan showing the region of the body in which the void is located (in this case, the lumbar spine). FIG. 6(b) shows the void identified on a 2D slice of the patient data. FIG. 6(c) shows a 3D model of the void superimposed on the MRI scan, and FIG. 6(d) shows a 3D model of the solid void extracted by this technique.

Figure 7:
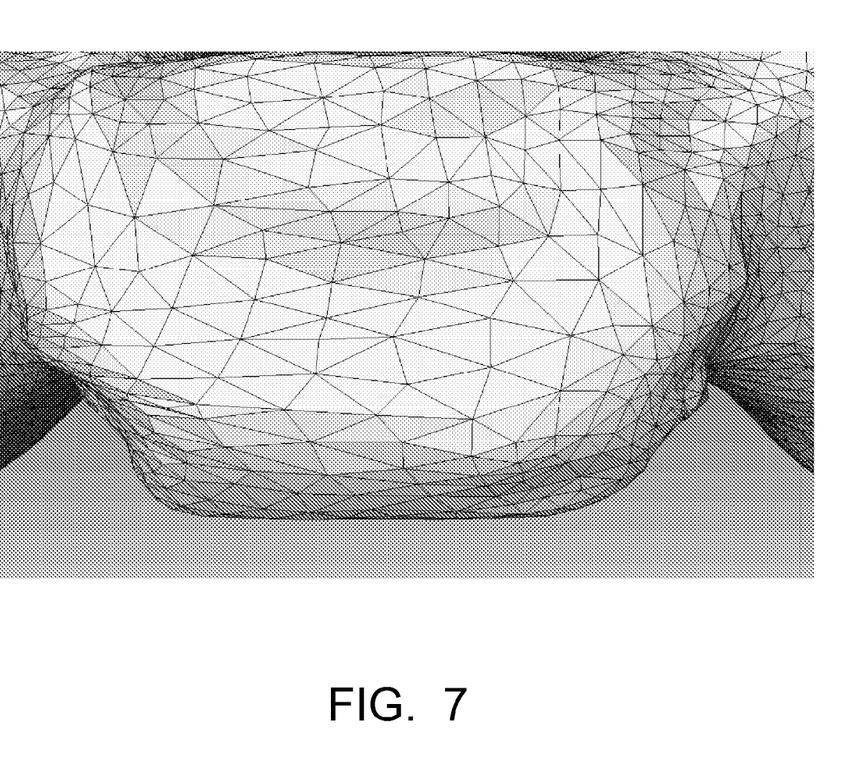
FIG. 7 is a surface representation of a solid model extracted by a void geometry extraction process of the present invention.

FIG. 7 provides a visual representation of solid model data generated by computer imaging software. This type of surface representation is known in the rapid prototyping art, and the surface is defined by a plurality of triangular surfaces. The surface definition defines the nodal coordinates of each node of each triangle. Nodal connectivity is also provided, as is a vector that is normal (perpendicular) to the triangle surface.

A computer program is used to identify and extract the surface of the void geometry that is normal to patient anatomy. The dot product between the normal vector of each triangle of the void surface and a vector in the direction of interest is computed. If the dot product is greater than a specified value, then the triangle of the void surface is extracted. If the dot product is less than a specified value, then the triangle is rejected. When this process is complete for all triangles in the dataset the surface of interest is identified and extracted. The "specified value" used to accept or reject triangles may vary depending on the particular geometry of a void involved in a given application of the above-described method. With respect to a fusion cage of the present invention, for example, an exemplary specified value is 0.8. In the fusion cage example, the dot product is used to extract only the surface that is in contact with the vertebral end plate. Assuming a vector is created that points straight up from the surface of the void, the surface that is to be extracted, 0.8 is a suitable value. The values of the dot product range from −1 to 1, with −1 indicating a surface pointing in the opposite direction and 1 indicating a surface pointing in the same direction. Since the surface is curved, a threshold is needed near 1 that will extract the top surface of the void but not the sides or bottom. A value lower than 0.8, for example, would extract not only the top surface but at least a portion of the side surfaces as well. Depending on the particular void desired to be extracted for a given application, a different value can be used to extract only the desired surfaces.

Figure 8:
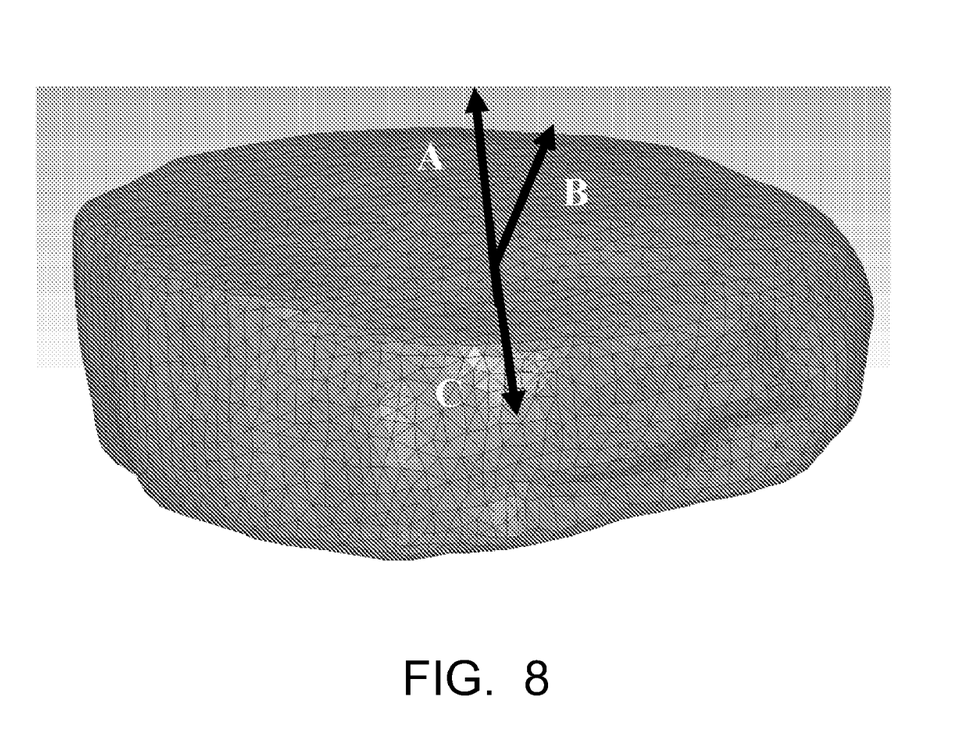
FIG. 8 a representation of a surface extraction in accordance with the present invention.

FIG. 8 is a visual representation of surface extraction showing vectors A, B, & C thereon. The dot product of vector A and B is a measure of the length of the component of vector A in the direction of vector B. This is used to determine which triangles that make up the void surface are in the direction of interest. In the illustration provided in FIG. 8, the dot product of A and C is negative since the two vectors point in opposite directions. The dot product between A and B, however, is positive. The closer the two vectors are to pointing in the same direction, the larger the magnitude of the result. In this way, triangles that are normal to patient anatomy are identified, and those that are not normal are eliminated from the dataset. Each triangle, for example, has an outward normal vector associated with it (i.e. a vector pointing away from the triangular surface and perpendicular to it). Using this data, the orientation of every triangle that makes up the void surface can be known. In the example of a fusion cage, the orientation of each triangle is compared with that of the vertebral end plate. In order to determine which triangles are facing the end plate surface and which are not, a vector is created perpendicular to the end plate. The dot product of this vector is then compared with the dot product of the outward normal vector of each triangle on the surface. The dot product for each triangle on the top surface will be greater than the 0.8 threshold described above, whereas the dot product for triangles on the side and bottom will be below the threshold. If the void were a cube, for example, and it was desired to extract the top surface, a vector would be created that points straight up from the top surface of the cube. Next, a dot product would be determined between an outward normal vector on each cube face and the reference vector extending straight up from the top surface of the cube. The top surface of the cube would have a dot product of 1, the side surfaces would have a dot product of 0 since they are perpendicular to the top surface, and the bottom surface would have a dot product of −1.

Figure 9:
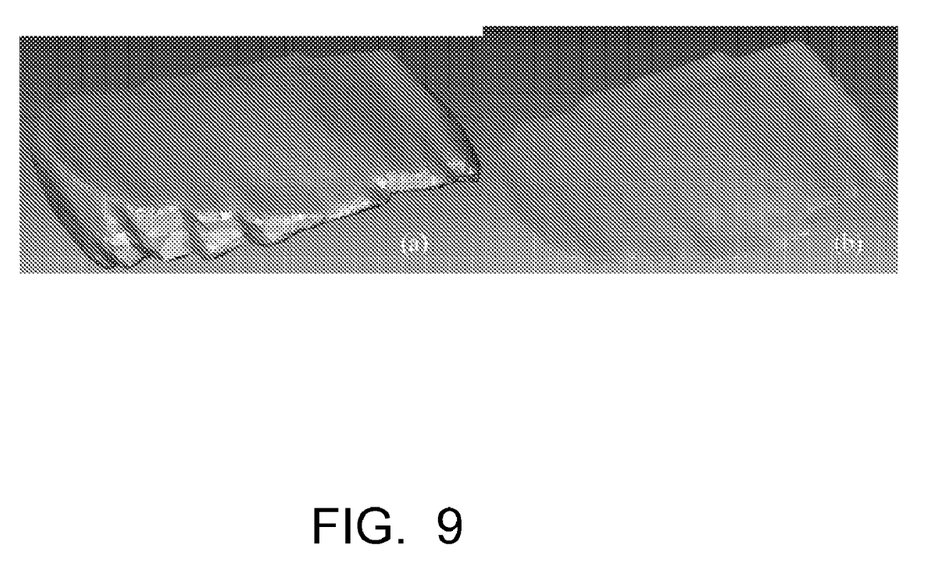
FIG. 9 is a representation of a void solid model and superior surface extracted in accordance with the teachings of the present invention.
Figure 10:
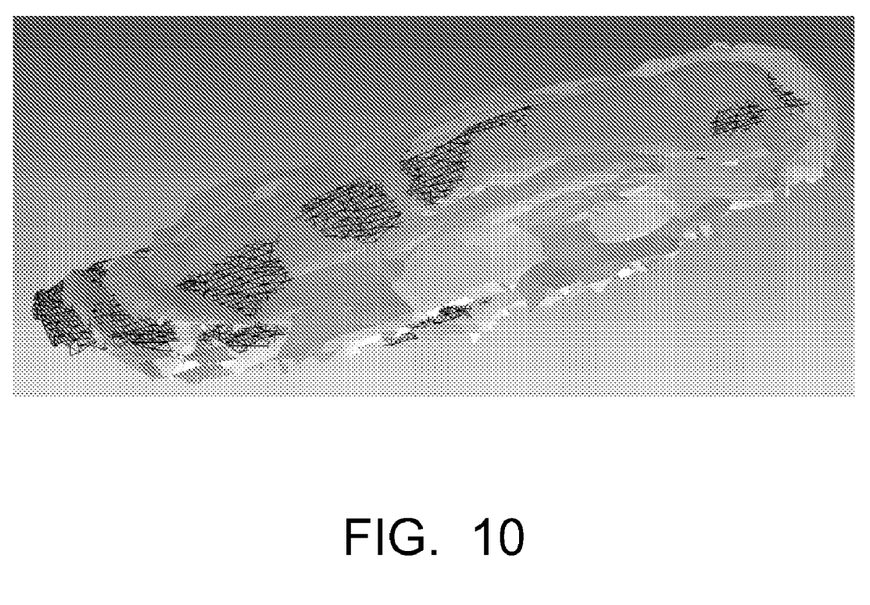
FIG. 10 is a representation of a surface overlay procedure in accordance with the present invention.
Figure 11:
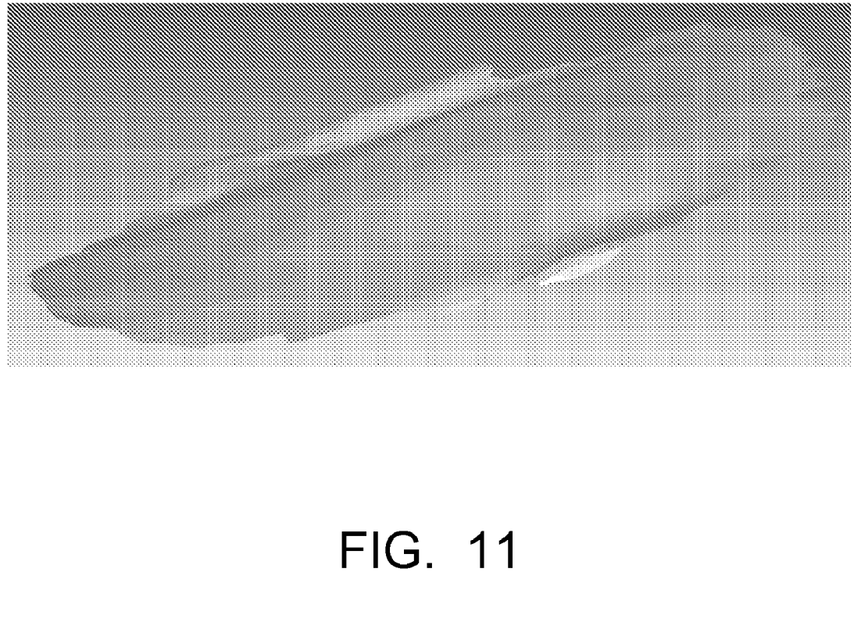
FIG. 11 is a representation of an interpolated surface in accordance with the teachings of the present invention.

FIG. 9 shows a void solid model and the superior surface extracted by the present method. The void solid model is provided in FIG. 9(*a*), whereas the superior surface extracted is provided in FIG. 9(*b*). Once the surface of interest has been extracted, a computer program is used to apply coordinate transformation to the surface data. This transformation translates and rotates all of the surfaces to overlay them with one another. FIG. 10 provides an illustration of the surface overlay procedure, showing several surfaces overlaid with one another. Various surfaces in the figure have been shaded differently so that the combination can be seen more clearly.

Once the surfaces are overlaid, a computer program is used to apply an interpolation algorithm that averages the surface data into one 'universal' surface that can be used for the surgical implant. The surface provided may be used further in a computer-aided design (CAD) package for design of the surgical implant.

It should be understood that the various descriptions and illustrations of the present system set forth herein are exemplary and are not intended to limit the scope of the present invention. Upon reading this disclosure, many variations and modifications will be apparent to those of skill in the art, and it is contemplated that these variations and modifications are within the spirit and scope of the present invention.

We claim:

1. A fusion cage comprising:
   a first housing portion;
   a second housing portion; and
   an insert portion adapted to be inserted in an insertion direction between said first and second housing portions such that said first and second housing portions are held in place by said insert portion, the insert being slidingly engaged by said first and second housing portions,
   wherein an external geometry of said fusion cage corresponds substantially to a geometry of a void in which said fusion cage is to be inserted; and
   further wherein said first and second housing portions each include a stop, said stop extending substantially perpendicularly from one of said housing portions toward the other of said housing portions when said insert portion is received therebetween, said stop of each of said housing portions cooperating to prevent said insert portion from extending in said insertion direction beyond an outer edge of said fusion cage.

2. The fusion cage according to claim 1 wherein each of said first and second housing portions comprises at least one aperture extending through a thickness thereof to allow bone growth through at least a portion of said fusion cage once said fusion cage has been implanted within a patient.

3. The fusion cage according to claim 1 further comprising at least one ridge extending across at least a portion of an exterior surface of at least one of said first and second housing portions, said ridge adapted to engage a surface within a patient's body, the surface being adjacent said fusion cage, in order to substantially prevent movement of said fusion once said fusion case is placed in operable position within said patient.

4. The fusion cage according to claim 1 wherein at least one of said first and second housing portions comprises a first lock portion, and further wherein said insert portion comprises a second lock portion, said first and second lock portions being adapted engage one another such that when said lock portions engage said insert portion is locked into position relative to said first and second housing portions.

5. The fusion cage according to claim 4 wherein said first lock portion is a groove and said second lock portion is a raised portion, said groove being sized and shaped to receive said raised portion, thereby locking said insert portion in place with respect to said first and second housing portions.

6. The fusion cage according to claim 4, wherein the other of said first and second housing portions includes another first lock portion, and said insert portion includes another second lock portion, said first and second lock portions being adapted to engage one another.

7. The fusion cage according to claim 1 wherein said insert portion defines an interior space therein for allowing bone growth within said interior space.

8. The fusion cage according to claim 7 wherein said interior space of said insert portion is sized and shaped to receive a plunger portion of a tool for inserting a fusion cage into a space between adjacent vertebrae.

9. A fusion cage comprising:
   a first housing portion;
   a second housing portion; and
   an insert portion adapted to be received between said first and second housing portions such that said first and second housing portions are held in place by said insert portion, the insert being slidingly engaged by said first and second housing portions,
   wherein an external geometry of said fusion cage corresponds substantially to a geometry of a void in which said fusion cage is to be inserted; and
   further wherein each of said first housing portion includes a first lock portion, said second housing portion includes a second lock portion and said insert portion includes a third lock portion and a fourth lock portion, said first and third lock portions adapted engage one another and said second and fourth lock portions adapted to engage one another such that when said lock portions engage said insert portion is locked into position relative to said first and second housing portions, said first and third lock portions and said second and fourth lock portions each including a groove and a raised mating portion extending in the direction of sliding engagement.

10. The fusion cage of claim 9, wherein said first and third lock portions and said second and fourth lock portions are each configured for engagement perpendicular to the direction of sliding engagement between said insert portion and said first and second housing portions.

* * * * *